(12) United States Patent
Huang et al.

(10) Patent No.: US 11,248,244 B2
(45) Date of Patent: Feb. 15, 2022

(54) SCHIZOCHYTRIUM LIMACINUM STRAIN, BUILDING METHOD THEREFOR AND APPLICATION THEREOF

(71) Applicant: Nanjing University of Technology, Nanjing (CN)

(72) Inventors: He Huang, Nanjing (CN); Lujing Ren, Nanjing (CN); Shenglan Chen, Nanjing (CN); Lingjun Geng, Nanjing (CN); Xiaojun Ji, Nanjing (CN); Xuechao Hu, Nanjing (CN)

(73) Assignee: Nanjing University of Technology, Jiangsu (CN)

( * ) Notice: Subject to any disclaimer, the term of this patent is extended or adjusted under 35 U.S.C. 154(b) by 0 days.

(21) Appl. No.: 16/607,861

(22) PCT Filed: May 10, 2017

(86) PCT No.: PCT/CN2017/083764
§ 371 (c)(1),
(2) Date: Oct. 24, 2019

(87) PCT Pub. No.: WO2018/205165
PCT Pub. Date: Nov. 15, 2018

(65) Prior Publication Data
US 2020/0190545 A1    Jun. 18, 2020

(51) Int. Cl.
*C12P 7/64* (2006.01)
*C12N 1/14* (2006.01)
*C12R 1/645* (2006.01)

(52) U.S. Cl.
CPC ............ *C12P 7/6427* (2013.01); *C12N 1/145* (2021.05); *C12R 2001/645* (2021.05)

(58) Field of Classification Search
None
See application file for complete search history.

(56) References Cited

U.S. PATENT DOCUMENTS 6,566,583 B1 * 5/2003 Facciotti .................. A61P 3/10
800/281
7,214,853 B2 * 5/2007 Facciotti .................. A61P 3/02
800/281

FOREIGN PATENT DOCUMENTS

CN    102741267 A    10/2012
CN    104974944 A    10/2015

OTHER PUBLICATIONS

Sahin et al. (AMB Expr., 8:7, pp. 1-8, 2018).*
Li, Huiling et al. ("A High-DHA Production Strain of Schizochytrium sp. Through Mutagenesis"), (Food Science and Technology), vol. 40, No. (9), Dec. 31, 2015 (Dec. 31, 2015), ISSN: 1005-9989, pp. 12-16, see entire document.
Zhuang, Xiaoyan et al. ("Establishment of Genetic Transformation System of Schizochytrium sp. by Homologous Recombination"), (Acta Microbiologica Sinica), vol. 55, No. (4), Apr. 4, 2015 (Apr. 4, 2015), ISSN: 0001-6209, pp. 510-517, see entire document.
Zhao, Xiaowei et al. ("Thraustochytrids and Their Biosyntheses of Docosahexaenoic Acid"), (Journal of Wenzhou Normal College (Natural Science Edition)), vol. 25, No. (5), Oct. 30, 2004 (Oct. 30, 2004), ISSN: 1006-0375, pp. 90-94, see entire document.
Feng, Yun et al. ("Effects of Culture Media on Docosahexaenoic Acid Production by Schizochytrium sp."), (Chinese Journal of Bioprocess Engineering), vol. 11, No. (5), Sep. 30, 2013 (Sep. 30, 2013), ISSN: 1672-3678, pp. 26-31, see entire document.

* cited by examiner

*Primary Examiner* — Hope A Robinson
(74) *Attorney, Agent, or Firm* — Proi Intellectual Property US; Klaus Michael Schmid (57) ABSTRACT

Provided is a *Schizochytrium limacinum* strain, a building method therefor and an application thereof. The strain disclosed is classified and named as *Schizochytrium* sp. HX-RS, and the preservation number is CCTCC NO: M2017046. An acyltransferase functional domain originating from *Shewanella* PKS enzyme is adopted instead of an acyltransferase functional domain originating from *Schizochytrium* sp. PKS enzyme, and the strain is obtained by performing flat panel screening and acclimation screening with a high rotation seed and a low temperature.

1 Claim, 4 Drawing Sheets

Specification includes a Sequence Listing.

SCHIZOCHYTRIUM LIMACINUM STRAIN, BUILDING METHOD THEREFOR AND APPLICATION THEREOF

CROSS REFERENCE TO RELATED APPLICATION

The present application is the US national stage of International Patent Application PCT/CN2017/083764 filed on May 10, 2017.

FIELD OF THE INVENTION

The invention belongs to the biochemical engineering field, in particular to a method for producing oil by utilizing microorganisms, specifically a *Schizochytrium* sp. strain capable of fermenting and co-producing DHA and EPA.

BACKGROUND OF THE INVENTION

EPA and DHA are omega-3 long chain polyunsaturated fatty acids which are very important for human growth and development, and have the efficacy of reducing blood lipid, improving intelligence, and preventing and treating some diseases, such as hypertension, arteriosclerosis, cardiovascular diseases, senile dementia, anti-inflammation and anti-cancer. These fatty acids can reduce triglyceride level in serum by activating nuclear peroxisome proliferator-activated receptors (PPARs), thus regulating the transportation, storage and metabolism of oil in many tissues. It is difficult for the human body to meet the body's demand for EPA and DHA through own synthesis, so EPA and DHA should be ingested from food.

At present, EPA and DHA are mainly obtained from deep sea fish. The sustainable supply of fish oil is affected by region and climate, as well as fish diseases and overfishing, so the production and quality of fish oil are unstable. Moreover, the marine pollution is increasingly serious, and the residual pollutants in fish bodies are serious, e.g., methylmercury. The purification process is complicated and the cost is high. Fish oil has peculiar fishy smell and many impurities, and can be easily oxidized, which is difficult to meet the demand of food additive industry. Therefore, finding a new source of EPA and DHA has become the focus of single cell oil research. The currently used DHA producing strain is *Schizochytrium* sp., and EPA producing bacteria are *Shewanella* sp. and *Photobacterium profundum* respectively.

*Schizochytrium* sp. is currently the main industrial strain of DHA-rich oil, with fast growth rate. The cell dry weight of *Schizochytrium* sp. is 200 g/L, the proportion of lipid in cell dry weight is 70%, its DHA content accounts for about 42% of total fatty acids, and DPA content accounts for about 20%, but EPA content is less than 1%. At present, the EPA has not been subject to large-scale industrial fermentation production. The biomass of several commonly used EPA producing bacteria is lower than that of *Schizochytrium* sp., for example, the biomass of *Shewanella* sp. 717 only reaches 6.2 g/L after the fermentation, the biomass of *Mortierella alpine* ATCC32222 reaches 20 g/l after fermentation for 384 h, and the highest biomass of *Pythium splendens* RBB-5 only reaches 42.5 g/l.

At present, the effect of changing the proportion of unsaturated fatty acids in *Schizochytrium* sp. through the optimization and fermentation control of culture medium is minimal, especially the EPA content cannot be controlled. How to control the distribution of unsaturated fatty acids and the quality of lipid in the strain by other means has become an urgent problem to be solved.

*Schizochytrium* sp. is synthesized to form long-chain polyunsaturated fatty acids through PKS enzyme. This pathway is independent of the classic fatty acid elongation and desaturation pathway. It is catalyzed by polyketone synthase, a complex enzyme that is independent of oxygen, located in cytoplasm and composed of many structural domains. The expression of polyketone synthase is controlled by the coordination of several functional structural genes. Acyltransferase (AT) is one of the important functional domains, which can identify and transfer fatty acyl groups in ACP domain during polyunsaturated fatty acid synthesis and plays an important role in the enrichment of fatty acids and the synthesis of polyketide.

In addition, oxygen and temperature have important effects on the growth of *Schizochytrium* sp. and the synthesis of long-chain polyunsaturated fatty acids. Hyperoxia is beneficial to the growth of *Schizochytrium* sp. during fermentation, but is not good for DHA accumulation. Low temperature is beneficial to the accumulation of polyunsaturated fatty acids in *Schizochytrium* sp., but not good for the growth of the strain. The invention provides a study method for reforming polyketide synthase synthesized by polyunsaturated fatty acids, and obtaining mutant strains with improved fatty acid ratio by replacement of functional domains, and screening a strain capable of producing two polyunsaturated fatty acids of EPA and DHA through selection at high rotation speed and low temperature.

SUMMARY OF THE INVENTION

The purpose of the invention is to overcome the problems of the prior art and provide a *Schizochytrium* sp. strain capable of producing two polyunsaturated fatty acids of EPA and DHA with high output.

In order to achieve the technical purpose, the invention adopts the following technical solution:

A *Schizochytrium* sp. strain, which is classified and named as *Schizochytrium* sp. HX-RS, has been preserved in China Center for Type Culture Collection (CCTCC) on Feb. 20, 2017 at Luojiashan, Wuchang, Wuhan City, with preservation number of CCTCC NO: M2017046. The deposits were made and accepted under the Budapest Treaty and applicants aver under 37 CFR § 1.808(a) that the deposit was made under conditions that assure that:

(1) Access to the deposit will be available during pendency of the patent application making reference to the deposit to one determined by the Director to be entitled thereto under § 1.14 and 35 U.S.C. § 122, and (2) Subject to paragraph (b) of this section, all restrictions imposed by the depositor on the availability to the public of the deposited material will be irrevocably removed upon the granting of the patent.

The invention also provides a construction method of the strain, comprising the following steps:

(1) taking *Schizochytrium* sp. HX-308 as an original strain, knocking out the acyltransferase domain (AT) in the genome of the original strain, and introducing the acyltransferase domain (AT) of an exogenous strain to build a recombinant strain;

wherein the exogenous strain is *Shewanella* sp. (SCRC-2738);

(2) performing selection on a recombinant strain constructed in step (1) at a rotation speed of 180-250 rpm and a temperature of 18-25° C., and screening the strain with high growth speed and high unsaturated fatty acid content.

The acyltransferase domain described in the invention is a catalytic domain with a specific function which has not been fully confirmed. What can be confirmed is that such domain plays an important role in the synthesis process of microbial fatty acids. It is preliminarily judged that it has fatty acyl group capable of recognizing ACP domain, and it is transferred into cell fluid and released as free fatty acid, or is transferred to CoA and changed to fatty acyl CoA. It is predicted that the catalytic domain can also inosculate different acyl groups CoA (e.g., acetyl CoA, propionyl CoA, except malonyl CoA) to synthesize different polyketides.

For the method of the invention for knocking out the acyltransferase domain (AT) in the genome of the original strain in step (1) is to knock out the gene of the acyltransferase domain (AT) in the genome of *Schizochytrium* sp. by taking the upstream and downstream of the acyltransferase domain (AT) as homologous recombination fragments and the bleomycin-resistant gene expression cassette as a screening marker.

Wherein the nucleotide sequence of the upstream homologous arm of the acyltransferase domain (AT) is shown as SEQ ID NO:1, and the nucleotide sequence of the downstream homologous arm of the acyltransferase domain (AT) is shown as SEQ ID NO:2.

The method for introducing the acyltransferase domain (AT) of the exogenous strain in step (1) is to build homologous recombination fragments containing the expression cassette of the Shew-AT gene by taking the upstream and downstream regions of the acyltransferase domain (AT) as homologous recombination fragments, and the expression cassette of the Shew-AT gene sequentially contains a ubiquitin promoter, the Shew-AT gene and a ubiquitin terminator; and the nucleotide sequence of the Shew-AT gene is shown in SEQ ID NO:3.

In step (1), the homologous recombination fragment is introduced into *Schizochytrium* sp. by electrotransformation. Wherein the electrotransformation parameters are 0.5-0.8 KV, 150-200Ω and 45-55 μF.

In step (2), the selection mode of the recombinant strain comprises:

Screening on the resistant plate containing zeocin, and transferring the screened recombinant strain into the shake flask, one generation every 24 hours, 30-50 generations in total;

wherein the concentration of zeocin in the plate is 15-45 μg/mL.

The invention also provides the application of the strain HX-RS in the co-production of EPA and DHA. Lipid containing EPA and DHA can be obtained through fermentation by using the strain.

In the invention, the inventor found that *Schizochytrium* acyltransferase (AT) can affect the types of fatty acids by knocking out the AT functional domain of the *Schizochytrium* sp. The obtained AT knock-out strain has small and fragile cells, and grows extremely slow, and the content of DPA and DHA in total fatty acid is reduced to 12.51% and 35.20% from the original 19.87% and 49.52% respectively. On this basis, AT on the genome of *Schizochytrium* sp. is replaced with an expression box with a strong promoter and exogenous acyltransferase (Shew-AT), and the constructed strain has the characteristics of fast growth and increased unsaturated fatty acid content after being domesticated at high rotation speed and low temperature, and can be used for co-producing DHA and EPA.

The strain obtained by the method in the invention has stable physiological biochemistry and stable genetic nature. When the lipid containing DHA and EPA is produced through fermentation, the biomass reaches 115.34 g/L and the oil yield is up to 69.6 g/L. EPA and DHA contents account for 4.68% and 51.3% of the total fatty acids respectively.

BRIEF DESCRIPTION OF THE DRAWINGS

FIG. 1 shows the steps for constructing plasmid PBS-Zeo-AT.

FIG. 2 shows the steps for constructing plasmid PBZ-Shew-AT.

The biological material described in the invention is classified and named as *Schizochytrium* sp. HX-RS, and has been preserved in China Center for Type Culture Collection (CCTCC) at Wuhan university, at Luojiashan, Wuchang, Wuhan City, China on Feb. 20, 2017, with preservation number of CCTCC NO: M2017046.

DETAILED DESCRIPTION OF THE PREFERRED EMBODIMENTS

The media used in the following examples are as follows:

Seed media: glucose 30-60 g/L, yeast extract 2-4 g/L, sodium glutamate 8-15 g/L, $KH_2PO_4$ 2-5 g/L, $CaCl_2 \cdot 2H_2O$ 0.5-4 g/L/l, $MgCl_2$ 2-5 g/L, NaCl 10-20 g/L, KCl 1-4 g/L, $MgSO_4 \cdot 7H_2O$ 2-6 g/l, $FeCl_3$ 0.1-0.5 g/l.

Fermentation media: glucose 60-120 g/L, yeast extract 2-46 g/L, sodium glutamate 15-20 g/L, NaCl 15-20 g/L, $MgCl_2$ 2-5 g/L, $(NH_4)_2SO_4$ 2-8 g/L, $KH_2PO_4$ 3-6 g/L, KCl 1-4 g/L, $MgSO_4 \cdot 7H_2O$ 3-5 g/L and $FeCl_3$ 0.1-0.5 g/L.

Example 1

This example illustrates the biological material source information of the invention.

*Schizochytrium* sp. HX-308 has been preserved in China Center for Type Culture Collection (CCTCC), at Luojiashan, Wuchang, Wuhan City, with preservation number of CCTCC No.: M209059. The deposits were made and accepted under the Budapest Treaty and applicants aver under 37 CFR § 1.808(a) that the deposit was made under conditions that assure that:

(1) Access to the deposit will be available during pendency of the patent application making reference to the deposit to one determined by the Director to be entitled thereto under § 1.14 and 35 U.S.C. § 122, and (2) Subject to paragraph (b) of this section, all restrictions imposed by the depositor on the availability to the public of the deposited material will be irrevocably removed upon the granting of the patent.

The domesticated *Schizochytrium* sp. HX-RS, a genetically engineered strain of *Schizochytrium* sp., is preserved in China Center for Type Culture Collection (CCTCC), at Luojiashan, Wuchang, Wuhan City, with the preservation number of CCTCC No: M2017046.

Vector PBS-Zeo: Constructed by this laboratory independently.

Vector PMD19-T (simple): Commercial vector, purchased from TaKaRa Company.

Example 2

This example illustrates the construction of a recombinant plasmid PBS-Zeo-AT for knock-out of AT functional domain.

Figure 1:
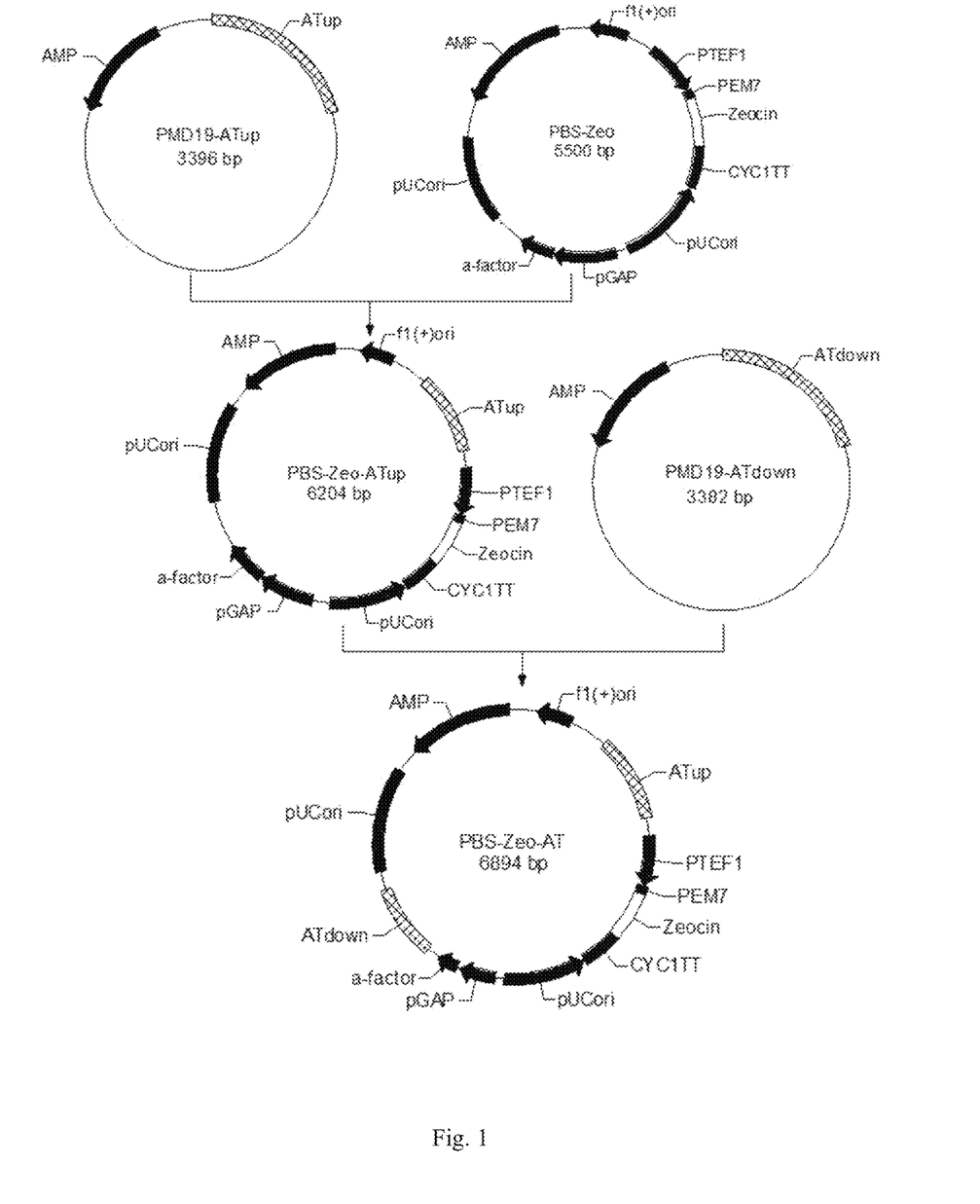

The steps for constructing the plasmid PBS-Zeo-AT are shown in FIG. 1.

1. Obtaining Upstream and Downstream Homologous Arms of an AT Gene of *Schizochytrium* sp.

(1) Obtaining an Upstream Homologous Arm of an AT Gene of *Schizochytrium* sp.

Designing primers ATup-s and ATup-A according to the AT gene sequence obtained through sequencing to amplify the upstream homologous arm of *Schizochytrium* sp. HX-308, and connecting such arm to a PMD19-T vector to obtain a recombinant plasmid pMD19-ATup. Wherein

```
ATup-S sequence:
5' AAGGAAAAAAGCGGCCGCTGCTATTCCGTGCTCCTCTC 3',

ATup-A sequence:
5' GCTCTAGAGCGCCTTGGGCGTGATGTTGAG 3'.
```

(2) Obtaining a Downstream Homologous Arm of an AT Gene of *Schizochytrium* sp.

Designing primers ATdown-S and ATdown-A according to the obtained AT gene sequence to amplify the downstream homologous arm, and connecting such arm to a pMD19-T vector to obtain a recombinant plasmid pMD19-ATdown.

```
ATdown-S sequence:
5' CCGGAATTCCGGTGGAACAAGGCTCTGGCCGT 3';

ATdown-A sequence:
5' CGGGGTACCCCGGACGCCAGGAACAAGGTGGG 3'.
```

2. Constructing a Plasmid PBS-Zeo-ATup

Performing double enzyme digestion on plasmids pMD19-ATup and PBS-Zeo by use of NotI and XbaI restriction incision enzymes respectively, and then connecting the gel-extracted ATup fragment to the linearized PBS-Zeo vector to obtain the recombinant plasmid PBS-Zeo-ATup.

3. Constructing a Plasmid PBS-Zeo-AT

Performing double enzyme digestion on plasmids pMD19-ATdown and PBS-Zeo-ATup by use of EcoRI and KpnI restriction incision enzymes respectively, and then connecting the gel-extracted ATdown fragment to a linearized PBS-Zeo-ATup vector to obtain the recombinant plasmid PBS-Zeo-AT.

Example 3

This example describes the production of oil by an acyltransferase AT-deficient *Schizochytrium* sp. Strain.

Performing double enzyme digestion on the plasmid PBS-Zeo-AT by use of two restriction incision enzymes NotI and KpnI, and then purifying fragments containing AT upstream and downstream homologous arms and bleomycin by a Takara gel extraction kit; transforming the fragments into *Schizochytrium* sp. HX-DS by electroproration; coating the transformed bacterial solution on a plate containing 20 µg/mL bleomycin, and culturing it in dark at 30° C. for 2 days; picking out positive single colony shake flask for culturing, extracting genome for PCR verification, and naming the correct defective bacterium *Schizochytrium* sp. HX-DS.

Figure 3:
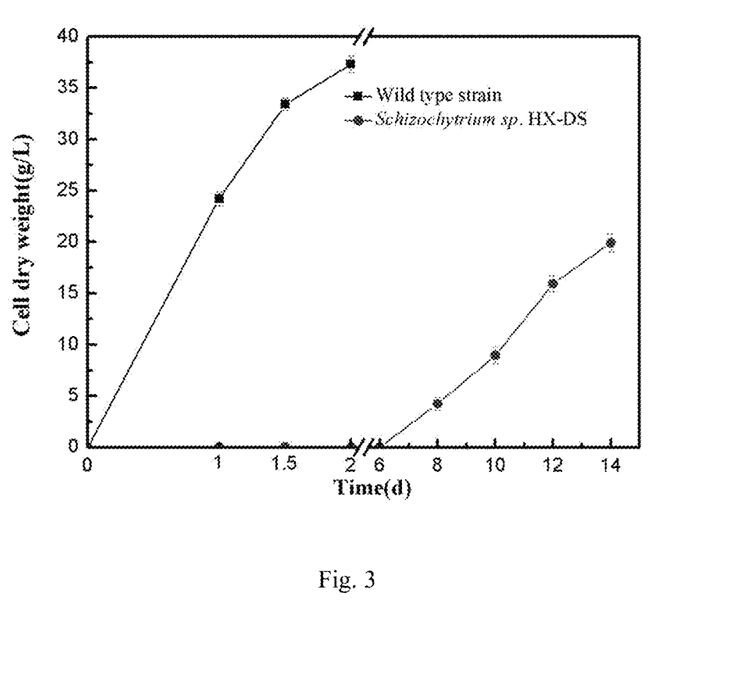
FIG. 3 shows the biomass changes of *Schizochytrium* sp. HX-DS and the original strain.

Inoculating the obtained engineering bacteria into seed media at a temperature of 30° C. and a rotation speed of 170 rpm, measuring cell dry weight and fatty acid content respectively, and comparing such parameters with those of the original strain under the same conditions. The results are shown in FIG. 3 and table 1.

TABLE 1

Comparison of distribution difference between fatty acids in seeds of *Schizochytrium sp.* HX-DS and the original strain

| Fatty acid | Composition of fatty acid/% | |
|---|---|---|
| (% TFA) | Original strain | *Schizochytrium sp.* HX-DS |
| C14:0 | 2.25 ± 0.26 | 10.24 ± 0.24 |
| C16:0 | 17.95 ± 0.25 | 32.96 ± 0.31 |
| C18:0 | 0.33 ± 0.02 | 0.72 ± 0.05 |
| EPA | 1.04 ± 0.02 | 1.13 ± 0.05 |
| DPA | 19.87 ± 0.14 | 12.51 ± 0.11 |
| DHA | 49.52 ± 0.23 | 35.20 ± 0.17 |

As shown in FIG. 3 and Table 1, due to the slow cell growth and reduced biomass after the knock-out of the AT gene of *Schizochytrium* sp., the biomass of the strain cultured for 14 days was only 1/2 of that of the original strain cultured for 2 days. DHA yield dropped from 49.52% to 35.20%.

This example describes the fact that the changes of the AT domain of *Schizochytrium* sp. can affect the fatty acid types of the strain.

Example 4 Construction of a Recombinant Plasmid PBZ-Shew-AT

Figure 2:
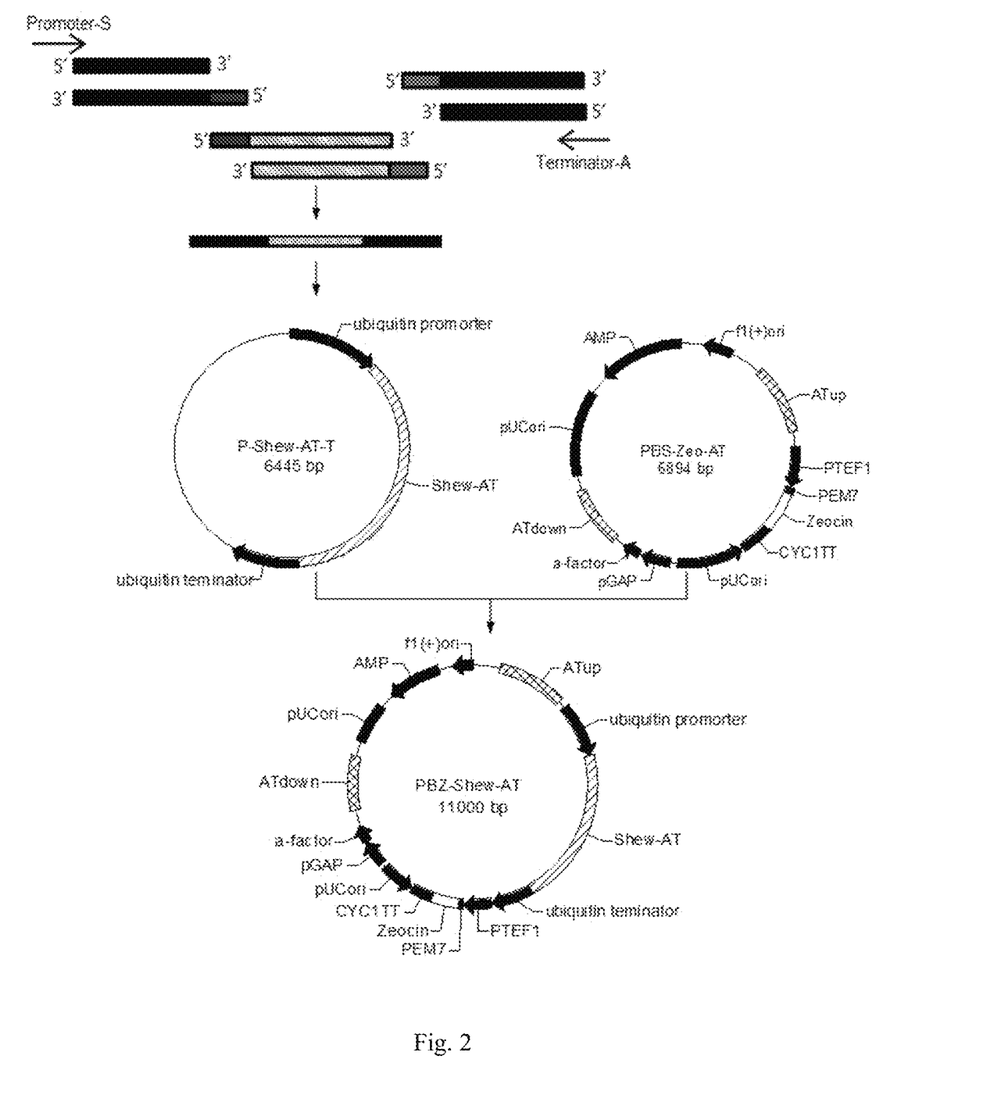

The steps for constructing the plasmid PBZ-Shew-AT are shown in FIG. 2.

1. Cloning a Ubiquitin Promoter, Shew-AT and a Ubiquitin Terminator

Referring to the ubiquitin promoter, SHEW-AT (AT gene of *Shewanella* sp. SCRC-2738) and ubiquitin terminator gene sequences in NCBI, which were synthesized by Suzhou Jinweizhi Biotechnology Co., Ltd., taking the synthesized plasmids pUC-Ubiquitin promoter, pUC-Shew-AT and pUC-Ubiquitin terminator as templates, and designing the following primer sequences to amplify three gene fragments:

```
Promoter-S:
5'GCTCTAGAGCCGTTAGAACGCGTAATACGACTCAC 3'

Promoter-A:
5'CCGAGGCCTTCGGCGTTTGCTCCACTTCGTCTTATCCTCAGTCATGTT
GG 3'

Shew-S:
5'CCAACATGACTGAGGATAAGACGAAGTGGAGCAAACGCCGAAGGCCTC
GG 3'

Shew-A:
5'TTAGTTTAGTCCGACTTGGCCTTGGTTAGACCTCACCCTGAAGGAGGT
```

-continued

GA 3'

Terminator-S:
5'TCACCTCCTTCAGGGTGAGGTCTAACCAAGGCCAAGTCGGACTAAACT
AA 3'

Terminator-A:
5'CGGGATCCACCGCGTAATACGACTCACTATAGG 3'

2. Fusing PCR to connect the ubiquitin promoter, Shew-AT and the ubiquitin terminator to construct a vector P-SHEW-AT-T. Splice the DNA fragment ubiquitin promoter, Shew-AT and ubiquitin terminator to obtain a three-gene splicing fragment through PCR fusion reaction, and connecting the obtained fragment with a pMD19-T(Simple) vector to obtain the recombinant plasmid P-SHEW-AT-T.

3. Constructing a Vector PBZ-Shew-AT

Performing double enzyme digestion on plasmids P-Shew-AT-T and PBS-Zeo-AT by use of XbaI and BamHI restriction incision enzymes respectively, and then connecting the gel-extracted Shew-AT gene expression cassette fragment to a place between the AT upstream homologous arm and bleomycin resistant gene fragment in PBS-Zeo-AT to construct the vector PBS-Shew-AT.

Example 5 Construction of SHEW-AT Substitute Schizochytrium sp Strain

Performing double enzyme digestion on the plasmid PBZ-Shew-AT by use of two restriction incision enzymes NotI and KpnI, and then purifying target fragments containing Shew-AT and bleomycin by a Takara gel extraction kit; transforming the fragments into Schizochytrium sp. by electroproration (parameters: 0.5-0.8 KV, 150-200Ω, 45-55 μF); coating the transformed bacterial solution on a plate containing 20 μg/mL bleomycin, culturing it in dark at 30° C. for 2 days; and picking out positive single colony shake flask for culturing, extracting genome for PCR verification, and naming the correct defective bacterium Schizochytrium sp. HX-RS0.

Figure 4:
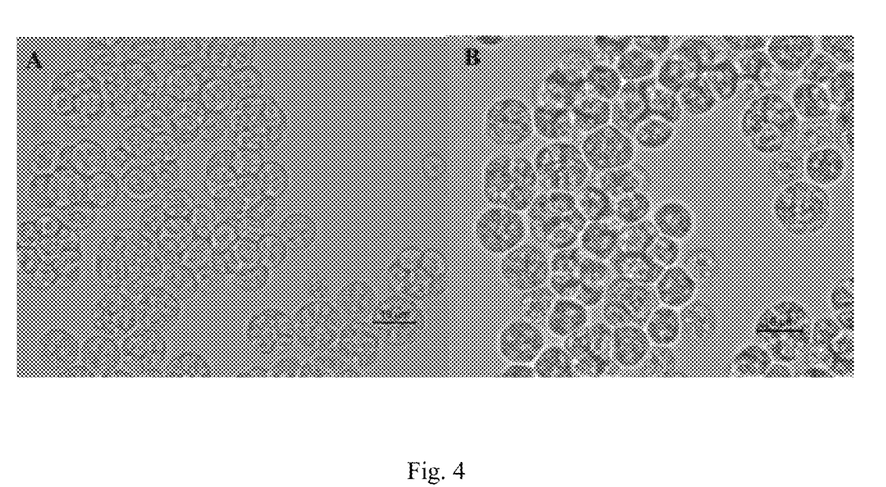
FIG. 4 is a morphological diagram of an original strain and B *Schizochytrium* sp. HX-RS0 cultured for 2 days.
Figure 5:
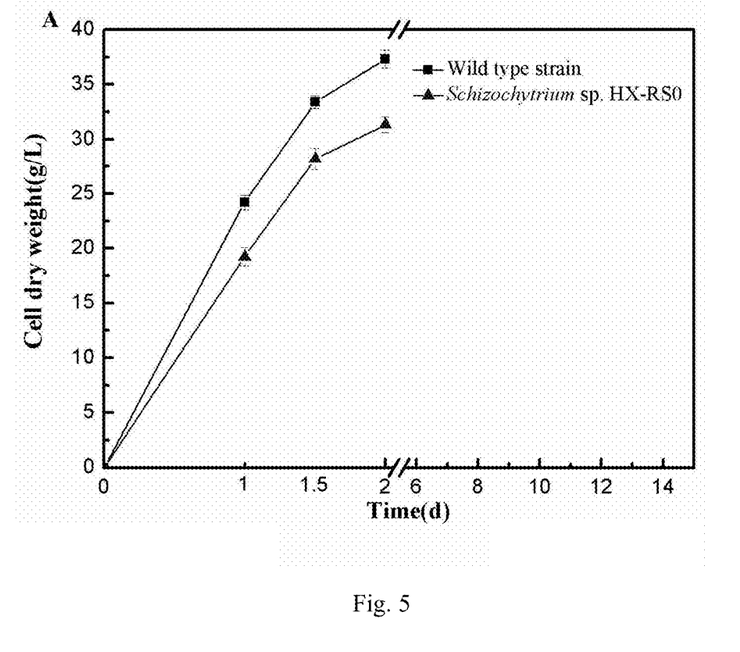
FIG. 5 shows the biomass changes of *Schizochytrium* sp. HX-RS0 and the original strain.

Inoculating the obtained engineering strain into seed media for investigation of the seed's properties at a temperature of 30° C. and a rotation speed of 170 rpm. Observing cell morphology, measuring the cell dry weight, and comparing the fatty acid content with that of the original strain under the same conditions. The results are shown in FIG. 4, FIG. 5 and Table 2.

The results show that Schizochytrium sp. HX-RS0 restored its growth, and its biomass reached 31.3 g/L after 2 days of culturing, which was still lower than that of the original strain. The cell morphology was uniform and petal-like, which was obviously superior to that of the original strain, and the EPA content of Schizochytrium sp. HX-RS0 reached 3.84%, 72.9% higher than that of the original strain. The DHA content was recovered from 35.2% to 47.2%, but slightly lower than that of the original strain.

Example 6 Selection of Shew-AT Substitute Schizochytrium sp. Strain

Domesticating the Shew-AT substitute Schizochytrium sp. HX-RS0 strain obtained in Example 5 at high rotation speed and low temperature, screening such strain on a resistant plate containing bleomycin, and transferring it to one generation every 24 hours, totally 30-50 generations. The concentration of zeocin in the plate is 15-45 μg/mL, the rotation speed for screening is 180-250 rpm and the temperature is 18-25° C.

Taking the biomass, DHA and EPA contents of the strain as assessment indexes, and screening out 20 strains with high DHA and EPA contents. The biomass, DHA and EPA contents of four strains (named and numbered as Schizochytrium sp.

HX-RS0-4, Schizochytrium sp. HX-RS0-6, Schizochytrium sp. HX-RS0-12 and Schizochytrium sp. HX-RS0-16 in sequence) were 10% higher than those of the original strain; fermenting 4 strains of domesticated strain for verification; culturing the 4 obtained strains in seed media for 3 generations, and then inoculating the seed solution into 100 mL fermentation culture medium with 10% (v/v) inoculation amount at a temperature of 30° C. and a rotation speed of 170 rpm; terminating the fermentation when 100 g/L glucose in the culture medium was exhausted; measuring the cell dry weight, oil content, and contents of DHA and EPA respectively; and comparing the fermentation parameters with those of the original strain and the undomesticated strains under the same conditions. The results are shown in Table 3.

TABLE 2

Comparison of distribution difference between fatty acids in seeds of Schizochytrium sp. HX-RS0 and the original strain (Percentage of total fatty acid content)

| Fatty acid | Composition of fatty acid/% | |
|---|---|---|
| (% TFA) | Original strain | Schizochytrium sp. HX-RS0 |
| C14:0 | 2.25 ± 0.26 | 6.61 ± 0.41 |
| C16:0 | 17.95 ± 0.25 | 22.83 ± 0.24 |
| C18:0 | 0.33 ± 0.02 | 0.48 ± 0.01 |
| C22:0 | 1.22 ± 0.08 | 0.95 ± 0.06 |
| EPA | 1.04 ± 0.02 | 3.84 ± 0.02 |
| DPA | 19.87 ± 0.14 | 13.64 ± 0.16 |
| DHA | 49.52 ± 0.23 | 47.2 ± 0.17 |

TABLE 3

Comparison of fermentation results between domesticated strain, original strain and undomesticated strain

| Strain | Fermentation parameter | | | | |
|---|---|---|---|---|---|
| | Biomass (g/L) | Oil content g/L | DHA content (%) | EPA content (%) | Fermentation time (h) |
| Original strain | 45.94 | 17.3 | 45.2 | 1.39 | 48 |
| *Schizochytrium sp.* HX-RS0 | 46.76 | 17.5 | 46.4 | 3.81 | 48 |
| *Schizochytrium sp.* HX-RS0-4 | 52.18 | 18.1 | 49.9 | 3.98 | 44 |
| *Schizochytrium sp.* HX-RS0-6 | 56.62 | 19.8 | 51.2 | 4.31 | 42 |
| *Schizochytrium sp.* HX-RS0-12 | 58.24 | 19.6 | 51.4 | 4.42 | 39 |
| *Schizochytrium sp.* HX-RS0-16 | 55.12 | 18.8 | 50.9 | 4.38 | 40 |

As shown in Table 3, comprehensive comparison shows that *Schizochytrium* sp. HX-RS0-12 strain was the most obvious strain of the four domesticated engineering bacteria, with higher biomass, oil content, and DHA and EPA contents. The obtained strain was named as *Schizochytrium* sp. HX-RS, which is the strain screened by the invention.

Example 7 Supplementary Fermentation of *Schizochytrium* sp. HX-RS 5 L Fermentation Tank Inoculating the final *Schizochytrium* sp. HX-RS seed solution into a sterilized 5 L fermentation tank containing 3 L fermentation medium at an inoculation amount of 10% (v/v); and taking silicone SE-2 as a defoaming agent during the fermentation process, and fermenting and culturing it for 5 days at a temperature of 30° C., an aeration ratio of 1 vvm and a stirring speed of 170 rpm. At the end of fermentation, the biomass and the oil output of the original strain were 102.71 g/L and 52.46 g/L respectively. EPA and DHA accounted for 1.41% and 44.9% of the total fatty acid respectively. EPA and DHA yields reached 0.78 g/L and 24.8 g/L respectively. The biomass and the oil output of HX-RS strain reached 115.34 g/L and 69.6 g/L respectively. EPA and DHA accounted for 4.68% and 51.3% of the total fatty acid respectively. EPA and DHA outputs reached 3.32 g/L and 36.4 g/L respectively. It can be seen that, compared with the original strain, the oil content increased by 32.67%, the EPA and DHA contents increased by 69.9% and 14.3%, respectively, and the EPA and DHA outputs increased by 76.3% and 46.8%, respectively.

What is claimed is:

1. A *Schizochytrium* sp. strain, wherein the *Schizochytrium* sp. strain is classified and named as *Schizochytrium* sp. HX-RS with a preservation number of CCTCC NO: M2017046.

* * * * *

SEQUENCE LISTING

<160> NUMBER OF SEQ ID NOS: 3

<210> SEQ ID NO 1
<211> LENGTH: 704
<212> TYPE: DNA
<213> ORGANISM: Artificial Sequence
<220> FEATURE:
<223> OTHER INFORMATION: Nucleotide Sequence of the Upstream Homologous
      Arm of the Acyltransferase Domain

<400> SEQUENCE: 1

```
tgctattccg tgctcctctc cgaagccgag ggccactacg agcgcgagaa ccgcatctcg      60
ctcgacgagg aggcgcccaa gctcattgtg cttcgcgccg actcccacga ggagatcctt     120
ggtcgcctcg acaagatccg cgagcgcttc ttgcagccca cgggcgccgc cccgcgcgag     180
tccgagctca aggcgcaggc ccgccgcatc ttcctcgagc tcctcggcga gacccttgcc     240
caggatgccg cttcttcagg ctcgcaaaag cccctcgctc tcagcctcgt ctccacgccc     300
tccaagctcc agcgcgaggt cgagctcgcg gccaaggggta tcccgcgctg cctcaagatg     360
cgccgcgatt ggagctcccc tgctggcagc cgctacgcgc ctgagccgct cgccagcgac     420
cgcgtcgcct tcatgtacgg cgaaggtcgc agcccttact acggcatcac caagacatt      480 caccgcattt ggcccgaact ccacgaggtc atcaacgaaa agacgaaccg tctctgggcc     540
gaaggcgacc gctgggtcat gccgcgcgcc agcttcaagt cggagctcga gagccagcag     600
caagagtttg atcgcaacat gattgaaatg ttccgtcttg gaatcctcac ctcaattgcc     660
ttcaccaatc tggcgcgcga cgttctcaac atcacgccca aggc                      704
```

<210> SEQ ID NO 2
<211> LENGTH: 690

```
<212> TYPE: DNA
<213> ORGANISM: Artificial Sequence
<220> FEATURE:
<223> OTHER INFORMATION: Nucleotide Sequence of the Downstream
      Homologous Arm of the Acyltransferase Domain

<400> SEQUENCE: 2
tggaacaagg ctctggccgt tgaatttaat gcgctgcgcg aggcctgggg cattccacag     60
agtgtcccca aggacgagtt ctggcaaggc tacattgtgc gcggcaccaa gcaggatatc    120
gaggcggcca tcgccccgga cagcaagtac gtgcgcctca ccatcatcaa tgatgccaac    180
accgccctca ttagcggcaa gcccgacgcc tgcaaggctg cgatcgcgcg tctcggtggc    240
aacattcctg cgcttcccgt gacccagggc atgtgcggcc actgccccga ggtgggacct    300
tataccaagg atatcgccaa gatccatgcc aaccttgagt tccccgttgt cgacggcctt    360
gacctctgga ccacaatcaa ccagaagcgc ctcgtgccac gcgccacggg cgccaaggac    420
gaatgggccc cttcttcctt tggcgagtac gccggccagc tctacgagaa gcaggctaac    480
ttcccccaaa tcgtcgagac catttacaag caaaactacg acgtctttgt cgaggttggg    540
cccaacaacc accgtagcac cgcagtgcgc accacgcttg gtccccagcg caaccaccdtt    600
```

```
cccaacaacc accgtagcac cgcagtgcgc accacgcttg gtccccagcg caaccacctt    600
gctggcgcca tcgacaagca gaacgaggat gcttggacga ccatcgtcaa gcttgtggct    660
tcgctcaagg cccaccttgt tcctggcgtc                                     690

<210> SEQ ID NO 3
<211> LENGTH: 2343
<212> TYPE: DNA
<213> ORGANISM: Artificial Sequence
<220> FEATURE:
<223> OTHER INFORMATION: Nucleotide Sequence of the Shew-AT Gene

<400> SEQUENCE: 3
gtggagcaaa cgccgaaggc ctcggccatg ccctccgta ttgcgctcat tctcctcccc     60
accccgcagt ttgaggtcaa cagcgtcgat cagtcggtgc tcgccagcta ccagacccctc   120 cagcccgagc tcaatgccct cctcaacagc gcgcccaccc ccgagatgct cagcattacc    180
atctcggacg acagcgatgc caattcgttc gagtcgcaac tcaacgcggc cacgaatgcg    240
atcaataacg gctacatcgt gaaacttgcc acggccaccc acgccctcct catgcttccg    300
gcgctcaagg ccgcgcagat gcgtatccac ccgcatgccc aactcgccgc catgcagcag    360
gcgaaaagca cccccatgag ccaggtctcg ggtgagctca agctcggcgc caacgcccdtt    420
```

```
agcctcgccc agacgaacgc cctcagccat cgctcagcc aggccaagcg caatctcacc    480
gacgtctcgg tgaacgaatg tttcgagaac ctcaagagcg agcagcaatt cacggaggtg    540
tactcgctca ttcagcagct tgcgtcgcgt acccatgtgc gcaaggaggt caaccagggt    600
gtcgaactcg gtcccaagca ggccaagtcg cactactggt tcagcgagtt ccatcagaac    660
cgcgtcgccg cgatcaactt tatcaatggc cagcaggcga cgtcgtacgt gctcacgcag    720
ggctcgggtc ttctcgccgc gaagagcatg cttaatcagc agcgcctcat gttcatcctc    780
cccggcaact cgcagcagca aattacggcg tcgattacgc agcttatgca gcagctcgaa    840
cgcctccagg tgacggaggt caacgaactt tcgctcgagt gccagcttga gctcctctcg    900
attatgtacg ataacctcgt caacgcggac aagcttacga cccgcgactc gaaacccgcg    960
taccaggcgg tgatccaagc ctcgtcggtg tcggcggcca agcaggaact ttcggccctc   1020
aacgatgccc tcaccgcgct ctttgccgag cagaccaacg cgacgagcac gaacaagggt   1080
ctcatccagt acaagacccc cgccggcagc taccttaccc tcaccccct cggctcgaac   1140
```

```
aacgacaacg cccaggccgg tctcgcgttc gtgtaccccg gtgtcggcac cgtctatgcg    1200
gacatgctca acgagctcca ccagtacttt cccgcccttt acgcgaagct cgagcgcgag    1260
ggcgatctca aagccatgct ccaggccgaa gacatctatc acctcgatcc caagcacgcc    1320
gcgcaaatgt cgctcggcga tctcgccatt gccggcgtcg gctcgtcgta cctccttacc    1380
cagctcctca cggacgaatt caacatcaaa ccgaacttcg ccctcggtta ctcgatgggt    1440
gaggcgtcga tgtgggcgtc gctcggtgtc tggcagaatc cccatgccct catctcgaaa    1500
acccagaccg accccctctt tacctcggcg attagcggca agctcaccgc ggtccgtcag    1560
gcctggcagc tcgacgatac ggccgccgag atccagtgga actcgttcgt ggtgcgctcg    1620
gaggccgcgc ccatcgaggc ccttctcaag gactatcccc acgcctacct cgcgatcatc    1680
cagggcgaca cgtgtgtgat cgcgggctgt gaaattcagt gtaaggccct cctcgccgcg    1740
ctcggtaaac gcggcatcgc ggccaatcgt gtgaccgcca tgcacaccca gccggccatg    1800
caggagcacc agaacgtcat ggacttctac ctccaacccc tcaaggcgga gcttccgtcg    1860
gagatctcgt tcatttcggc cgcggacctt acggccaagc aaaccgtgtc ggagcaggcc    1920
cttagctcgc aggtggtcgc ccagtcgatt gcggacacct tttgccagac gctcgacttc    1980
accgcgctcg tgcaccacgc ccaacatcaa ggcgcgaagc tctttgtgga gatcggcgcc    2040
gaccgtcaga actgcaccct catcgacaaa attgtgaaac aggacggcgc cagcagcgtc    2100
cagcatcagc cctgctgtac cgtgcccatg aacgccaagg gcagccagga tatcacctcg    2160
gtcatcaagg cgcttggtca gctcatctcg catcaggtcc cgctctcggt gcaacccttt    2220
atcgacggcc tcaagcgcga actcaccctc tgccagctta cctcgcagca gctcgcggcc    2280
cacgcgaatg tcgattcgaa gttcgagtcg aaccaggatc acctccttca gggtgaggtc    2340
taa                                                                  2343
```